United States Patent [19]

Larson et al.

[11] 4,251,220
[45] Feb. 17, 1981

[54] APPARATUS FOR AND METHOD OF DETERMINING HIGH PRESSURE, HIGH TEMPERATURE FEEDWATER CONTAMINANTS

[76] Inventors: Thurston E. Larson, 706 La Sell Dr.; Russell W. Lane, 1207 Devonshire Dr.; Chester H. Neff, 1808 Broadmoor Dr., all of Champaign, Ill. 61820

[21] Appl. No.: 955,972

[22] Filed: Oct. 30, 1978

[51] Int. Cl.[3] .................... G01N 27/02; G01N 33/18; G05D 9/00
[52] U.S. Cl. .............................. 23/230 R; 23/230 A; 210/662; 210/664; 422/68; 422/76; 422/106
[58] Field of Search .................. 23/230 R, 230 A; 422/68, 76, 106; 210/25, 26, 33; 324/30 R

[56] References Cited

U.S. PATENT DOCUMENTS

| | | | |
|---|---|---|---|
| 2,617,766 | 11/1952 | Emmett et al. | 210/25 |
| 2,832,673 | 4/1958 | Larson et al. | 422/68 X |
| 3,158,444 | 11/1964 | Larson et al. | 210/33 X |
| 3,495,943 | 2/1970 | Kapff | 210/25 X |
| 3,897,213 | 7/1975 | Stevens et al. | 210/25 X |

Primary Examiner—Michael S. Marcus
Attorney, Agent, or Firm—Charles H. Brown

[57] ABSTRACT

Apparatus of high sensitivity and accuracy for detecting and measuring very low levels of chlorides, sulfates, phosphates and nitrates in high pressure, high temperature feedwater present in once-through and supercritical boilers, nuclear reactors and cogeneration systems. A sample of feedwater at 350° F. and above is maintained near atmospheric boiling point in a vented chamber where volatile gases, mainly carbon dioxide, are removed by venting. The effluent from this chamber passes through a flow-type conductivity cell, is cooled to 20°-40° C. and flows upward through a hydrogen exchange resin bed at a flow rate of approximately 250 and 1,000 ml/min and higher. Subsequent reboiling of the condensate in a reboil chamber with the help of a small orifice valve through which a part of the hot feedwater sample passes provides constant temperature control of the condensate at or near atmospheric boiling and at a constant level prior to flow through another flow-type conductivity cell. This last cell measures the conductivity of the chlorides, sulfates, phosphates and nitrates in the converted acid form and indicates the extent of the contaminants of the foregoing substances in the feedwater. A recorder electrically connected to both cells enables observation of the difference in conductivity between the two cells, thereby providing an approximation of the amine or ammonia content in the high pressure, high temperature feedwater. Individual small orifice valves control the volume and rate of flow of the feedwater supplied to both the vented and reboil chambers.

7 Claims, 2 Drawing Figures

APPARATUS FOR AND METHOD OF DETERMINING HIGH PRESSURE, HIGH TEMPERATURE FEEDWATER CONTAMINANTS

This invention relates to a method of and apparatus for detecting and measuring low levels of chloride, sulfate, phosphate and nitrate in high pressure feedwater at atmospheric boiling temperatures.

BACKGROUND OF INVENTION

The capability of detecting and continuously measuring low levels of chloride, sulfate, phosphate and nitrate has been needed for water treatment control in the power industry for many years. The available titration or colorimetric procedures are not continuous measurements and have not possessed the necessary sensitivity or accuracy. So-called cation conductivity procedures have been used in the past as an indication of condensate leakage (inorganic comtamination) but, as with many such procedures, the errors involved with their use have not been fully recognized nor have corrective measures been applied to obtain precise results.

The use of once-through and supercritical boilers, pressurized water reactor (PWR) nuclear and cogeneration systems has brought to light problems of corrosion and deposits on surfaces of steam boilers and generators as a result of which stress-corrosion cracking of turbine blades and circulation troubles in the system occur, as in the denting (cracking) of Iconnel 600 in PWR heat exchangers. Chloride, sulfate, phosphate and nitrate in the high temperature feedwater, normally found in water, are responsible for this corrosion, for the harmful deposits, and for the deterioration of auxiliary equipment. Resulting mechanical failure, such as boiler tube eruption, may cause injury to operating personnel and serious economic disruption for the public.

The foregoing problem of stress corrosion cracking of turbine blades in large steam turbines has revealed an urgent need for reexamination of the allowable upper limits of steam purity. Heretofore, a maximum of 10–30 $\mu g/l$ (micrograms per liter) sodium (as $Na^+$), equivalent to 15–45 $\mu g/l$ chloride (as Cl), was considered allowable. Recently, turbine manufacturers have specified chloride ions plus sulfate ions ($Cl^- + SO_4^=$) limits of 5 $\mu g/l$ or less.

Corrosion studies have recognized the importance of $Cl^-$ and $SO_4^=$ ions in promoting the corrosion of metals in water. The measurement of the $Na^-$ (sodium) ion may not provide a correct estimate of anion contamination, as other cations such as potassium, calcium and magnesium may be present in combination with $Cl^-$ and $SO_4^=$ rather than $Na^+$ alone. Heretofore, the deleterious effect of calcium and magnesium impurities associated with chloride and sulfate has not been recognized or considered important in steam purity measurement. The recognition of such effect is important in the determination of feedwater contaminants, and is taken into account by the present invention.

So far as applicants are aware, the present invention achieves for the first time a greater sensitivity and accuracy of conductivity measurements based on chlorides, sulfates, and nitrates in feedwater than heretofore possible. The present invention is able to detect and continuously measure extremely low levels of 1 to 5 $\mu g/l$ (micrograms per liter) chlorides, sulfates and nitrates (equivalent to 0.6 to 3 $\mu g/l$ sodium). Heretofore, there has been no procedure for detecting chlorides, sulfates and nitrates at this very low level; still less, on a continuous measuring basis.

The apparatus of the present invention is designed to fill an analytical and operational need for control of contaminants and water treatment in large fossil fueled boilers, particularly once-through type or PWR (pressurized water reactor) nuclear systems. Up to the present time there has been no satisfactory method of continuous sampling and measuring the purity of saturated and superheated steam generated by these systems, due to the physical characteristics of the boiler design and the superheated steam used. Hence there is a present need to monitor the feedwater influent rather than the steam or steam condensate effluent. The present invention satisfies such need.

U.S. Pat. No. 3,158,444 granted Nov. 24, 1964 describes a method of and apparatus for determining steam purity. Although the apparatus illustrated therein bears a superficial resemblance to the apparatus of the present invention hereinafter illustrated and described it should be understood that the apparatus disclosed in the aforementioned patent is not designed for nor can it be used to test high temperature feedwater (approx. 350° F. and above) in place of steam. In using the apparatus of U.S. Pat. No. 3,158,444 for the determination of steam purity, it was found that the superheated steam deposits insoluble salts, such as sodium chloride and sulfate on the sampling line to the measuring instrument and in the instrument itself. This problem is described in an article entitled "The Prevention of Errors in Steam Purity Measurement Caused by Deposition of Impurities in Sampling Lines," by R. V. Cobb and E. E. Coulter published by the American Society for Testing Materials, Philadelphia, PA., Proc. ASTM61, 1386—1395 1961). The technique for avoiding these errors described in the foregoing article is complicated and has never been used practically, so far as applicants are aware. This problem does not exist in the practice of the present invention.

OBJECTS AND FEATURES OF INVENTION

An object of the present invention is to enable the continuous detection of low level chloride, sulfate, phosphate and nitrate of the order of 1-5 $\mu g/l$ in high pressure feedwater at atmospheric boiling temperatures from high pressure boiler systems and pressurized water reactor nuclear systems.

Another object is to improve the safety of high pressure steam generator systems that utilize high temperature, high pressure feedwater by detecting contaminating impurities in the feedwater which cause mechanical failures in the system.

A further object is to achieve accurate, sensitive and continuous measurements of chloride, sulfate and other anions in high temperature, high pressure feedwater at lower levels than heretofore possible.

A feature of the invention is the arrangement of a pair of conductivity cells in the flow paths of the water in the system which in cooperation with a recording instrument provides an indication of the effectiveness of the hydrogen exchange resin bed, thereby indicating to operating personnel when the resin should be replaced.

Another feature lies in the use of individually adjustable stainless steel valves having small orifices of approximately two-onehundredths of an inch for separately supplying the high pressure feedwater at atmospheric boiling temperature to coils in both the condenser and the reboil chamber. The metal from which the valves are made prevents possible contamination of the feedwater, such as may occur if copper or brass were used.

An advantage of the invention is that the apparatus can be used in the field where the power generating parts of the whole system are located, and does not require time consuming laboratory analytical methods involving huge samples by evaporation processes.

Other objects, features and advantages will appear from a reading of the following detailed description of the invention which is given in conjunction with a drawing.

DETAILED DESCRIPTION

Figure 1:
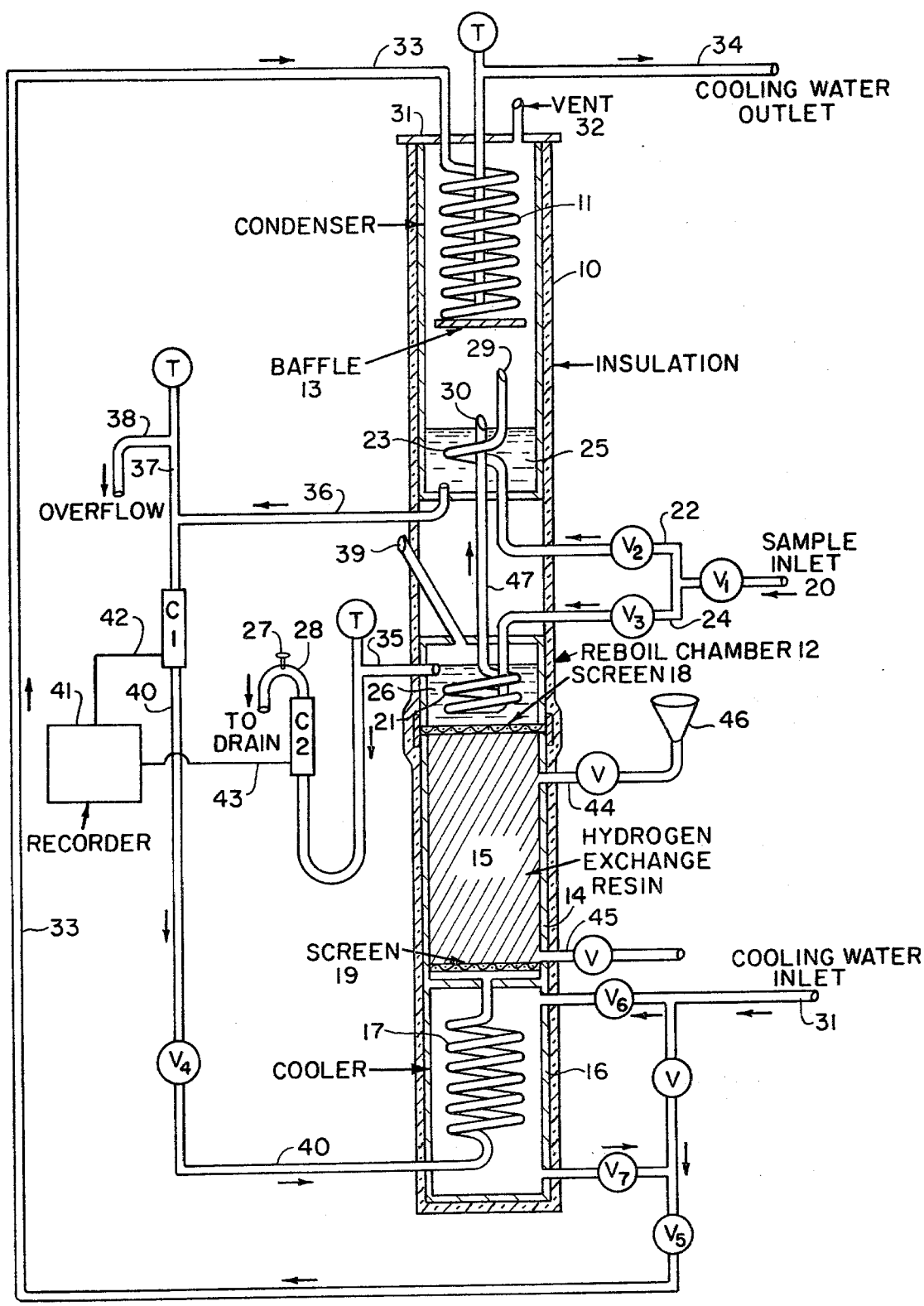
FIG. 1 is a vertical sectional view of the apparatus of the invention.

The apparatus of the invention comprises an elongated structure comprising tubular stainless steel sections 10, 12, 14 and 16 placed end-to-end to form a single integral structure. Section 10 is a water cooling condensing unit supported from section 12 by suitable metal braces or arcuate-shaped metal trusses. All sections are preferably of the same diameter. Upper section 10 contains a multi-turn cooling coil 11 and a disc-like baffle 13. Section 12 is a reboil chamber which is separated from section 14 by a screen 18 through which effluent from the section 14 may pass. Section 14 contains a hydrogen exchange resin bed 15. Bed 15 is, for example, a strong acid type cation exchange resin such as polystyrene material in hydrogen form sold by Rohm & Haas under the trade-name IR-120. This bed is of suitable depth to insure substantially complete exchange of the cations in the condensate to hydrogen ions. The metals used for sections 10, 12, 14 and 16 and the tubing therein are materials, such as stainless steel, which will not add contamination to the high temperature, high pressure sample feedwater supplied to the apparatus over sample inlet 20. The reboil chamber 12 and the screen 18 may suitably be clamped by collars or flanges to the lower chamber 14.

The cooling chamber 16 at the bottom of the apparatus contains a cooling coil 17, the upper end of which is in fluid communication with a perforated distributor plate 19.

A feedwater sample inlet pipe or tube 20 supplies high temperature feedwater under high pressure through a manually controllable valve V1, to a path divider arrangement 22, 24. Tubes 22 and 24 are provided with separate small orifice stainless steel manually controllable valves, V2 and V3 respectively, through which the high pressure, high temperature feedwater passes. These two valves which have orifices in the range of 0.01" to 0.02" are important in the practice of the invention. The temperature of the feedwater in chamber 10 is reduced to atmospheric boiling temperature.

Manually controllable valve V1 regulates the total flow of feed-water sample to the apparatus. Valve V3 regulates the amount of sample feedwater which passes to coil 21 in the reboil chamber 12, thereby regulating the heat which takes place in the reboil chamber. Manually controllable valve V2 serves a dual purpose, viz, (a) to by-pass some of the input feedwater sample into the coil 23 located within the condensing section 10 to maintain the temperature of the water of pond 25 at atmospheric boiling temperature, and (b) enables proper reboil without excessive boiling of the water 26 in the reboil chamber 12 due to the presence of coil 21 which receives high temperature feedwater through tube 24 and valve V3. Violent boiling of the water of pond 26 will cause a change in the water level of this pond and disturb the smooth constant flow of water through the tube 35. This constant flow is required for proper performance of the instrument. Thus both valves V2 and V3 together judiciously adjusted, regulate the operating temperatures of the water 25 and 26 in both condenser 10 and reboil chamber 12 at the same atmospheric boiling temperature despite variations in temperature and pressure in the input feedwater through valve V1, and maintain the flow of liquid through the resin bed constant.

The water 26 is at atmospheric boiling point, approximately 98.5° C., and is maintained at a constant level by the judicious adjustment of valves $V_2$ and $V_3$ to assure a constant flow of the water through conductivity cell $C_2$ at a rate of 250 ml/min to 1000 ml/min as described hereinafter. The constant level of the water 26 in the reboil chamber 12 is manually adjustable by raising or lowering waste or overflow tubing 28 which is attached to and communicates with the interior of cell $C_2$. It should be noted that the top of tube 28 is on the same horizontal line as tube 35. Cells $C_2$ and $C_1$ are flow-type conductivity cells which are well known in the art. An adjustable screw 27 passes through an opening in tubing 28 to prevent siphoning. The screw 27 may be replaced by an open-ended tube inserted into the top of tubing 28 to serve as a siphon breaker.

The feedwater exiting from valve V2 in the direction of the arrow over tube 22 and which is under pressure at a temperature of about 350° F. and higher, passes through coil 23 and discharge nozzle 29. The hot feedwater exiting from valve V3 in the direction of the arrow over tube 24 passes through coil 21 in the reboil chamber 12 and through an upwardly extending tube 47 to the discharge nozzle 30 in the section 10. Manually adjustable valves V1, $V_2$ and $V_3$ are important in the practice of the invention and have orifices in the range of 0.01" to 0.02" to prevent too much feedwater from passing therethrough. Both nozzles 29 and 30 serve to discharge their steam jets, if any steam is present therein, vertically for impingement upon the stainless steel baffle plate 13. Impingement baffle place 13 is slightly spaced from the wall of section 10 to permit an upward flow of discharged steam and gas which then pass out of section 10 through vent 32. Baffle 13 is supported by the bottom tubing of multi-turn coil 11. Coil 11 is supplied with cooling water from inlet 31 which communicates with tube 33 through an open and shut valve V5. An outlet tube 34 discharges the cooling water from the cooling coil 11. The coil 11 is suitably suspended from a closure plate 31'. Vent 32 in the closure plate serves to release any non-condensable gases such as $CO_2$ separated from the water in pond 25 and any steam exiting from nozzles 29 and 30 which pass by the baffle. This vent also helps to maintain the constant level of the water in pond 25 by preventing air finding. A tube 35 has an open end at the constant level of the water 26 in the reboil chamber. This pipe is in flow communication with the bottom of conductivity cell $C_2$, as shown. A tube 36 has an open end at the bottom of pond 25 for abstracting water therefrom and passing it through conductivity cell $C_1$. A short length of vertical tubing 37 supports a thermometer T at its upper end and has an overflow opening 38 placed at the constant level of pond 25. Any excess water from pond 25 passes out over overflow pipe 28. The level of the water in condensing section 10 (pond 25) must always be constant as determined by the level of the overflow pipe 38 which is at the same level. The flow rate of the feedwater in the sample inlet is such as to always produce an overflow in pipe 38 which maintains a constant level for pond 25. The constant level of pond 25 achieves a constant flow rate of liquid, via tube 40, into the coil 17 in the cooling chamber 16. In practice, the feedwater supplied by the sample inlet over tube 22 is mostly water which accumulates as pond 25 at the bottom of condensing section 10, although a small portion (about 5-10%) will produce flash steam from nozzle 29 and will be condensed by baffle 13 and fall back as water into pond 25.

The vertical tubing 40 conducts the water flowing through the conductivity cell $C_1$ into the bottom end of coil 17 contained within the cooling chamber 16. A manually controlled open and shut valve V4 regulates the flow rate of hot water from the cell $C_1$ which passes through tube 40. The cooled water, cooled to a temperature below 65° C. and preferably between 20° C. and 40° C., is passed through the distributor plate 19 into the hydrogen exchange resin bed 15. The perforated distributor plate 19 serves not only to pass the upward flow of the cooled water into the section 14 but also for supporting the bed of ion exchange material 15. The screen 18 above the resin bed 15 serves to prevent any particles from the resin bed from rising in the effluent therefrom beyond the level of said screen into the reboil chamber 12.

A vent 39 leading to the reboil chamber is for the same purpose as the vent 32, namely to permit the escape of any non-condensable gases such as carbon dioxide, released by the reboiling of the condensate or by the heating thereof to the atmospheric boiling point. Vent 39 also serves to allow the steam produced by reboiling in the reboil chamber 12, an escape path to atmosphere, thereby preventing fluctuating sample flow rates and assisting in the flushing of the non-condensable gases from the reboil chamber. The coil 21 in the reboil chamber 12 provides the heat necessary to drive off substantially all of the carbon dioxide that may be dissolved in the condensate. Coil 21 and reboil chamber 12 are of sufficient size to reheat the effluent from the hydrogen ion exchange bed 15 back to atmospheric boiling temperature.

The cooling chamber 16 is supplied with constant temperature cooling water from the cooling water inlet 31. Valves V6 and V7 regulate the volume of the cooling water passing into and out from the cooling chamber 16. The water in inlet 31 may be in the range from near zero to 30° C. and should cool the hot feedwater in tube 40 to 20°-65° C., preferably in the range of 20°-40° C., approximately.

In some instances, such as when there is little flash steam or if the temperature of the water in pond 25 is less than atmospheric boiling temperature the cooling or condensing coil 11 in the section 10 can be eliminated entirely in which case the vent 32 will permit the passage of any steam exiting from nozzle 29. The elimination of coil 11 will make unnecessary the use of the cooling water feedback tube 33 together with the thermometer T located at the top of coil 11. Alternatively, two cooling inlets can be used, one for the lower chamber 16 and the other for the upper chamber 10 with separate shut off valves in each cooling inlet.

Flow type conductivity cells $C_1$ and $C_2$ are electrically connected to a conductivity recording instrument 41 via electrical connections 42 and 43 respectively. During normal operating conditions the difference in conductivities in the cells is an indication of the ammonia and/or amine concentrations as well as $CO_2$ in the feedwater sample (influent). This difference is an indication of the extent of removal of the substances in the feedwater sample which interfere with accurate and sensitive measurements of chloride and sulfate. When the difference in conductivities of the cells $C_1$ and $C_2$ approaches zero as indicated on the recorder 41, then the hydrogen exchange resin bed 15 should be replaced. The two valves V, V and the tubing 44 and 45 associated therewith and connected to the interior of section 14 are for the purpose of fast removal and replacement of the resin by means of water flow. The open funnel 46 aids in the replacement of resin. The recorder 41 can be of a type which prints out both conductivity values of the cells $C_1$ and $C_2$, or, if desired, the recorder can be of a type which subtracts the conductivity of pure water (0.82 $\mu$S/cm at 98.5° C.) from the conductivity measurement of cell $C_2$, thereby indicating the chloride and sulfate content. The recorder 41 may be provided with an alarm which becomes actuated in the presence of excessive contents of chloride and sulfate in the feedwater.

Suitable recording instruments and flow type cells useful in the practice of the present invention are manufactured and sold by Beckman Instruments of Fullerton, Calif. Valves V1, V2 and V3 used in the practice of the invention are type "Whitey Series 21" manufactured by Whitey Company of Oakland, Calif. These valves are made of stainless steel, resistant to erosion or corrosion by high velocity, high pressure, high temperature feedwater, and have limited dimension orifices of approximately 0.02" inner diameter. These valves are microregulating valves designed to handle a flow capacity of 250 ml/min to 1000 ml/min at pressures of from 500 to 3,000 psig (lbs per square inch gauge) or higher at temperatures from 250° F. to 600° F.

Figure 2:
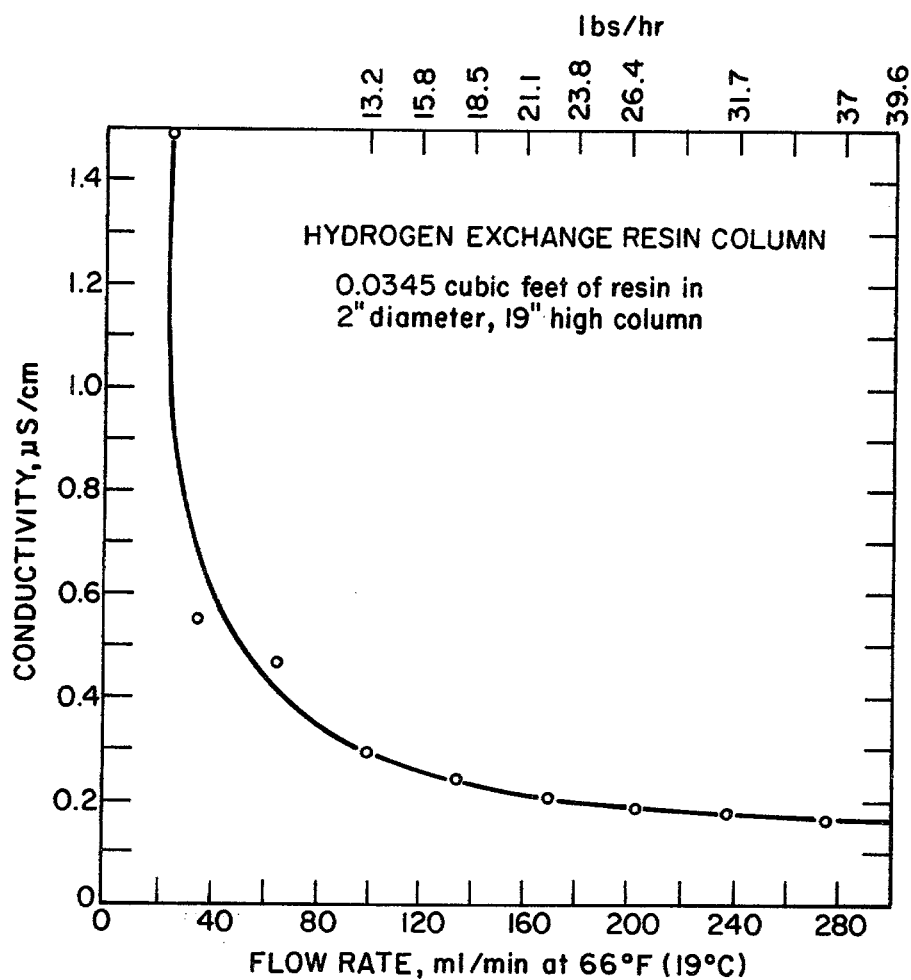
FIG. 2 graphically illustrates the effect of flow rate through the condensate analyzer on the conductivity of the effluent from the hydrogen exchange resin bed.

The effect of flow rates through the condensate analyzer of the invention on the conductivity of the effluent from the hydrogen resin bed is shown in the graphical representation of FIG. 2. We have satisfactorily operated the apparatus of the invention at a flow rate through the resin bed between 250 and 1000 ml/min at 20° C.-40° C. Higher flow rates can be used. Lower flow rates are less satisfactory because of higher background conductivity due to undesired resin leaching, as indicated on the graph. Other dimensions than those indicated in FIG. 2 and other conditions, such as temperature, will give other graphs, but all will show that at higher flow rates the conductivity will decrease.

In an embodiment of the invention built and successfully tested the apparatus was a circular construction with an overall height of approximately 4½ feet and with an outer diameter of approximately 4 inches. The stainless steel outer tube was approximately one-eighth (⅛") thick. A tubular brace eight and one-half inches (8½") long fastened the upper section 10 to the reboil chamber section 12. Upper section 10 had a height of eleven inches (11"); reboiler chamber 12 had a height of seven inches (7"); the resin chamber 14 was thirteen and three-quarter inches (13¾") high and the lower cooler section was eleven and one-quarter inches (11¼") high. Coil 11 in the condenser section had six turns, while coil 17 in the cooler section 16 had thirteen turns. The analyzer of the invention (the outer metal tubing) was surrounded by ½ inch fiber glass insulation to reduce heat losses and to maintain a constant control of temperature. It is preferred that the apparatus not be exposed to cold drafts. Beckman Instrument flow type conductivity cells and a Beckman Instrument recorder were used. The valves V1, V2 and V3 were Whitey Series 21 stainless steel of approximately 0.02" inner diameter. Stainless steel parts and "Mirprene" tubing have demonstrated their superior properties after adequate rinsing. By means of the invention, cell $C_2$ has been able to measure the conductivity of the chlorides and sulfates in the converted acid form (converted by the hydrogen exchange resin) as a precise determination of the degree of contamination of chlorides and sulfates in the feedwater sample. The analyzer of the invention is sensitive to 1–5 $\mu g/l$ of $Cl^{-1}$ or $SO_4^=$. This is equivalent to 0.6 to 3.0 $\mu g/l$ sodium, as contrasted to the results achieved in the aforementioned U.S. Pat. No. 3,158,444 used for determining steam (not feedwater) and restricted to a detection of approximately 3 $\mu g/l$ sodium.

The feedwater analyzer of the invention was tested at Kincaid Station, a mine mouth power station which is generally operated as a base load plant to supply electricity to the Chicago area. Its facilities include two once-through boilers operated at a pressure of 2620 psig (lbs per square inch gauge) and a temperature of 1005° F. and two 600 MW (megawatt) turbines. Cooling water is supplied by a man-made lake, Lake Sangchris. The apparatus of the invention was installed in a vertical position sampling feedwater from the economizer inlet of unit 1. The feedwater was passed to the top section 10 of the apparatus of the invention to relieve pressure and to reduce the 400° F. feedwater temperature to atmospheric boiling temperature. Part of the feedwater flow passed through the reboil chamber 12 to heat the entering resin-treated feedwater which had been cooled to reduce contamination from resin leaching. The effluent 26 from the resin bed 15 after being heated in the reboil chamber to atmospheric boiling water temperature to boil off carbon dioxide of the acidic feedwater resulting from passage through the hydrogen exchanger and to maintain constant atmospheric boiling temperature was then passed through conductivity cell $C_2$ mounted in the effluent line 35 from this reboil chamber, at which time the conductivity was recorded. In passage through the hydrogen exchanger, the ammonia and alkaline amines are removed and the cations of the feedwater salts (such as sodium of sodium sulfate) are replaced by hydrogen ions. The conductivity of ammonia and the amines is thereby eliminated by their removal. The mineral chlorides, sulfates and phosphates are converted to the respective mineral acids. Since the conductivity of hydrogen ions is about seven times that of metallic ions, the sensitivity of this conductivity measurement for minerals is significantly increased by measurement at constant boiling water temperature and by elimination of carbon dioxide and amine interference.

By using the present invention and assuming a 3 million lbs/hr feedwater flow (6000 gpm) at Kincaid Station, a detection of 0.1 gpm (gallons per minute) condenser leak (0.0016%) of lake cooling water would be indicated by a 0.033 $\mu S/cm$ increase in conductivity over that of purewater at 98.5° C. Even less than 0.033 $\mu S/cm$, for example 0.01 $\mu S/cm$, can be indicated by our analyzer apparatus. So far as we are aware, no other known instrumentation can achieve these results in a continuous measurement in a once-through boiler. The tests at the Kincaid Station with the apparatus of the invention achieved sensitive observations at low levels of chloride, sulfate, phosphate and nitrate which could not be as accurately detected by heretofore known instrumentation. We are thus able to detect and record anion levels as low as 1 $\mu g/l$.

What is claimed is:

1. Purity analyzer apparatus for continuously monitoring and measuring low levels of chloride, sulfate, phosphate and nitrate, of the order of 1–5 $\mu g/l$ in high pressure feedwater having a temperature of 350° F. and above, comprising means defining an upper chamber, means defining a reboil chamber below said upper chamber, means for supplying a sample of said high presure feedwater at a temperature of 350° F. and above and at a flow rate between 250 ml/min/and 1000 ml/min to both said upper and reboil chambers over separate paths, an adjustable small orifice regulating valve having an opening which is in the approximate range of 0.01" to 0.02" in each of said paths, a bed of hydrogen exchange resin below said reboil chamber and separated therefrom by a screen through which effluent from said bed can flow, a perforated water distributor plate at the bottom of said resin bed, first and second flow-type conductivity cells, means defining a water flow path from the lower part of said upper chamber to said first cell, a cooling chamber having a hollow cooling coil one end of which communicates with the bottom of said resin bed through said distributor plate and the other end of which communicates with said first cell, whereby water passing from said first cell to said resin bed is cooled, an adjustable valve located between said other end and said first cell for regulating the flow rate through said resin bed, means defining a water flow path from said reboil chamber to said second cell, and conductivity recording and indicating means electrically connected to both cells.

2. Analyzer apparatus for continuously monitoring and measuring low levels of chloride, sulfate, phosphate and nitrate of the order of 1–5 $\mu g/l$ in high pressure feedwater having a temperature of approximately 350° F. and above, comprising means defining an upper condensing chamber, means defining a water reboil chamber below said upper chamber, separate tubular coils in said chambers, a tubular path divider having two paths which respectively couple to the two coils in said upper chamber and said reboil chamber, an inlet for supplying a sample of said high pressure feedwater to said path divider construction at the junction of said two paths, a bed of hydrogen exchange resin below said reboil chamber and separated therefrom by a screen through which effluent from said bed can flow, a perforated water distributor plate at the bottom of said resin bed, means defining water flow path from said upper chamber to said resin bed through said distributor plate, and an adjustable valve in each of two paths of said tubular path divider and also in said inlet, each of said valaves having an orifice in the range of 0.01" and 0.02", the adjustments of said valves and the size of said reboil chamber and the size of said coils being chosen to maintain the water in said upper and reboil chambers at atmospheric boiling temperature and at constant levels; and conductivity measuring means coupled to the output of said reboil chamber.

3. Analyzer apparatus according to claim 2, including separate flow-type conductivity cells in the outputs from said upper and reboil chambers for measuring the conductivities of the water in said chambers.

4. Purity analyzer apparatus according to claim 2, wherein said upper chamber is approximately 11" high and contains a cooling coil having six turns, and reboil chamber is approximately 7" high, said resin chamber is enclosed in a chamber which is approximately 13¾" high, and said cooling chamber is approximately 11¼" high and has a coil therein of 13 turns, all of said chambers being circular and having a diameter of approximately 4".

5. Purity analyzer apparatus having a bed of hydrogen exchange resin, means for supplying to said bed a sample of feedwater to be tested at a flow rate between 250 and 1000 ml/min and higher at a temperature between 20° C. and 40° C., means defining a reboil chamber, means for passing the effluent from said bed into said reboil chamber, means for boiling in said reboil chamber the effluent from said bed, said last means including an adjustable micro regulating valve having an orifice in the range of 0.01" to 0.02", and means for maintaining the level of said effluent in said reboil chamber constant despite variations in temperature and pressure of said feedwater, means passing a portion of said boiled effluent through a conductivity cell, and means including a recorder electrically coupled to said cell.

6. The method of detecting and continuously measuring low levels of chloride, sulfate and nitrates of the order of 1-5 μg/l in high pressure feedwater having a temperature of 350° F. and above in large fossil-fueled boilers, which comprises obtaining a sample of the high pressure feedwater being fed to the boilers, and supplying the sample at a flow rate in the approximate range of 250 to 1000 ml/min through a first restricted orifice in the range of 0.01" to 0.02" and then through separate parallel-arranged second and third orifices also in the range of 0.01" to 0.02" to individual liquid communication paths, cooling the feedwater in one of said paths to a temperature of approximately 20° C., passing the cooled water through a bed of cation exchange material at a flow rate of about 250 ml/min to 1000 ml/min, subjecting the effluent from said bed of cation exchange material to heat from the feedwater in the other liquid communication path to heat said effluent to atmospheric boiling temperature, and measuring the conductivity of the heated effluent while maintaining the level of said heated effluent constant.

7. The method of determining the purity of high pressure, high temperature feedwater having a temperature between 350° F. and 600° F. which comprises passing a cooled sample of the feedwater through a bed of cation exchange material at a constant flow rate of about 250 ml/min to 1000 ml/min, passing an uncooled sample of the high temperature feedwater through an orifice in the range of 0.01" to 0.02" to heat the effluent from said bed to atmospheric boiling temperature while maintaining constant the level of the heated effluent, measuring the conductivity of the cooled feedwater before it is passed through said bed of cation exchange material with the conductivity of the heated effluent, and comparing said respective conductivities and recording the difference in said conductivities.

* * * * *